US007766826B2

(12) United States Patent
Lee et al.

(10) Patent No.: US 7,766,826 B2
(45) Date of Patent: Aug. 3, 2010

(54) MULTI-LEVEL AVERAGING SCHEME FOR ACQUIRING HEMODYNAMIC DATA

(75) Inventors: Brian B. Lee, Golden Valley, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1025 days.

(21) Appl. No.: 10/723,364

(22) Filed: Nov. 26, 2003

(65) Prior Publication Data

US 2005/0113647 A1 May 26, 2005

(51) Int. Cl.
*A61B 5/00* (2006.01)

(52) U.S. Cl. .................. 600/300; 600/508; 600/523

(58) Field of Classification Search ................ 600/300, 600/481, 483–486, 508–526, 500–504, 301; 607/23–26
See application file for complete search history.

(56) References Cited

U.S. PATENT DOCUMENTS

| 4,374,382 | A |   | 2/1983  | Markowitz       |         |
|-----------|---|---|---------|-----------------|---------|
| 5,331,966 | A | * | 7/1994  | Bennett et al.  | 600/508 |
| 5,355,891 | A | * | 10/1994 | Wateridge et al.| 600/515 |
| 5,743,267 | A | * | 4/1998  | Nikolic et al.  | 600/483 |
| 5,908,392 | A | * | 6/1999  | Wilson et al.   | 600/509 |
| 5,997,476 | A | * | 12/1999 | Brown           | 600/300 |
| 6,230,059 | B1| * | 5/2001  | Duffin          | 607/60  |

| 2002/0173829 | A1 | 11/2002 | Graindorge       |
|--------------|----|---------|------------------|
| 2003/0013974 | A1 | 1/2003  | Natarajan et al. |

FOREIGN PATENT DOCUMENTS

EP            1331022 A2    7/2003

OTHER PUBLICATIONS

Programmer User's Manual for the Model 10343 implantable monitor, Oct. 1993.

* cited by examiner

*Primary Examiner*—Henry M Johnson, III
*Assistant Examiner*—Kai Rajan
(74) *Attorney, Agent, or Firm*—Stephen W. Bauer (57) ABSTRACT

A system and method for storing and processing physiological data in a medical recording device that allows continuous data collection and storage of such data in multiple time-resolved levels are provided. The method includes: sampling one or more physiological signals at a selected sampling rate; deriving physiological parameter values from the sampled signal; storing the parameter values as they are determined in a temporary memory buffer for a predetermined storage interval; determining a statistical aspect of the stored parameter values upon expiration of the storage interval; and writing the statistical aspect to a long-term memory buffer. A number of long-term memory buffers may be designated for storing a statistical aspect of a physiological parameter at uniquely different time resolutions. The resolution of each long-term memory buffer is determined by the storage interval defined for an associated temporary memory buffer, which stores parameter values from which statistical aspects are computed.

7 Claims, 7 Drawing Sheets

MULTI-LEVEL AVERAGING SCHEME FOR ACQUIRING HEMODYNAMIC DATA

FIELD OF THE INVENTION

The present invention relates generally to the field of implantable medical devices used for monitoring physiological conditions. More particularly, the present invention is directed toward providing a method for acquiring and storing multiple levels of time resolved physiological data.

BACKGROUND OF THE INVENTION

Clinicians face a significant challenge in diagnosing and treating a medical condition characterized by transient symptoms, which may be influenced by changes in the disease state, patient activity, time of day, dietary influences, emotional influences, pharmaceutical side effects, etc. Diagnostic information available to a clinician is often limited to isolated clinical tests and examinations, which may or may not occur when a patient is symptomatic. Symptoms may gradually or suddenly worsen or improve over time making the physician's job in treating and diagnosing a condition even more difficult. Particularly in the field of cardiology, the mechanisms of such changes, for example in patients suffering from heart failure, are not fully understood. Acquisition of physiological data pertaining to a patient's medical condition on a continuous basis would be highly useful in diagnosing and treating individual patients and would provide valuable information for improving the medical understanding of disease mechanisms.

Ambulatory monitoring devices, such as a Holter monitor for studying a patient's ECG over an extended period such as 24 hours, are known. However, such ambulatory devices rely on patient compliance for collecting accurate data and are not generally tolerated for long periods of time such as weeks or months. Implantable medical devices are now available for acquiring and storing physiological data relating to a patient's medical condition over relatively long periods of time, such as one year or more. One such medical device is the Chronicle® Implantable Hemodynamic Monitor offered by Medtronic, Inc. The Chronicle device continuously senses a patient's EGM, intracardiac blood pressure signals, and an activity sensor signal and stores data in a looping memory whenever a data storage-triggering event occurs. Such data-storage triggering events may be related to a change in the patient's heart rhythm or a trigger delivered by the patient using an external hand-held device. The Chronicle device employs the leads and circuitry disclosed in commonly assigned U.S. Pat. Nos. 5,535,752 and 5,564,434, incorporated by reference herein, to record the EGM and absolute blood pressure values.

The patient may periodically download stored data to a home-based device for secure Internet transmission to Medtronic's Patient Management Network. A clinician may access the data at any time to view a continuous history of the cardiac data rather than the "snap shot" views normally obtained during office visits. Large amounts of physiological data collected during pertinent physiological or symptomatic events are made available to the clinician. The clinician, however, must now face the task of sorting through, analyzing and interpreting the large amounts of data, which may sometimes be an overwhelming task particularly in light of a clinician's large patient load.

Efficient recording of interesting aspects of physiological data has been desirable since ambulatory recording devices, both implantable and external, have first been used experimentally and clinically. Recording capabilities were introduced into implantable devices such as pacemakers and defibrillators after low power digital memory became implemented in these devices. Although the storage-to-size ratio of digital memory has increased with improved technology, storage of raw, uncompressed physiologic data, such as relating to ECG, blood pressure, oxygen saturation, body motion, respiration, blood flow, etc., is still not possible to achieve over a period of time longer than a day or so in small external, ambulatory recording devices and more particularly in small implantable devices.

Depending on the intended use, recordation of physiological data generally requires a sampling frequency of about 32 Hz or more. In some applications 100 Hz sampling or more is required. Approaches to reducing the memory requirements for storing physiological data include data compression methods, event-triggered data storage, data feature extraction methods, and data averaging.

Even when memory space is sufficient to store raw, uncompressed data, the data needs to be consolidated into a form that is usable and readily interpreted by the clinician. Consolidation of large amounts of stored data may be performed by an external computer after retrieval of the data from an implanted device. However, all-in-one storage and processing of data by an implanted device into a usable format that provides the physician with a clinically relevant view of the data would be more convenient than having to transfer and post-process data on another system.

As implantable device technologies improve, the available memory for storing physiological data has increased. Even so, the available memory within an implantable device is limited and therefore requires implementation decisions to be made regarding the time resolution of stored data and the length of a stored episode. If a detailed time resolution is desired, the duration of the recorded episode will be requisitely shorter. Physicians may desire to view varying resolutions of physiological data in order to analyze and understand the patient's condition over long-term, medium-term, and short-term trends. Having such data stored and immediately available by transferring the data from an implanted device to an external device can be convenient for the clinician in that the clinician is not required to download data from a remote website and match time and events of interest to large sets of data.

There remains a need, therefore, for a method and system for acquiring and storing physiological data in an efficient manner using a fixed amount of available memory in an implantable medical device or in an external ambulatory device having limited memory. Such a method preferably allows data to be stored in a way that permits a clinician to gain both long-term assessments of a patients disease status trends and detailed looks of recent or pertinent events.

SUMMARY OF THE INVENTION

The present invention provides a method for storing and processing physiological data in a medical recording device that allows continuous data collection and storage of such data in multiple time-resolved tiers. The method includes: sampling one or more physiological signals at a selected sampling rate; deriving physiological parameter values from the sampled signal; storing the parameter values as they are determined in a temporary memory buffer for a predetermined storage interval; determining a statistical aspect of the stored parameter values upon expiration of the storage interval; and writing the statistical aspect to a long-term memory buffer. A number of long-term memory buffers may be designated for storing a statistical aspect of a physiological signal at uniquely different time resolutions, the resolution of each long-term memory buffer being determined by the storage interval defined for an associated temporary memory buffer.

The present invention may be realized in a medical device capable of receiving one or more physiological signals and equipped with digital memory partitioned into a number of temporary memory buffers and a corresponding number of long-term memory buffers. Temporary memory buffers are provided physiological parameter values derived from a sampled physiological signal on a periodic basis. Long-term memory buffers are provided for storing statistical aspects of the stored physiological parameter values. The medical device further includes processing circuitry for computing one or more statistical aspects of the stored parameter values. The temporary buffers may be allocated to receive a number of parameter values received during a predetermined storage interval. The long-term memory buffers may be allocated to receive a given number of statistical data points corresponding to a given number of storage intervals. For a given physiological parameter derived from a sensor signal, multiple temporary and long-term memory buffers may be assigned for acquiring and storing statistical aspects of the physiological parameter at different temporal resolutions.

Two or more long-term memory buffers are designated for storing fine and coarse resolution data and optionally one or more intermediate levels of time-resolved data relating to a particular physiological parameter. Long-term memory buffers may be provided as looping memory buffers such that when a long-term memory buffer is full, the oldest statistical value is overwritten by the newest statistical value. The long-term memory buffers may be arranged serially such that a statistical value stored in a finer resolution long-term memory upon expiration of a storage interval becomes input to a temporary memory buffer associated with a coarser resolution long-term memory buffer. Alternatively, a number of temporary and corresponding long-term memory buffers may be arranged in parallel such that a temporary buffer associated with each long-term memory buffer receives input directly from sensor signal processing circuitry.

Selectable data storage configurations may be defined by a user according to the number of physiological parameters selected to be stored, the selected temporal resolutions of the stored parameters, and the duration of time that statistical data will be stored for each temporal resolution. The memory available within the implantable device for physiological data storage is automatically allocated for each parameter and time resolution selection wherein each selection affects the amount of memory remaining available for other parameter and time resolution selections. As such, the method for acquiring and storing physiological data includes automatic partitioning of the fixed amount of available memory according to selected data storage parameters and resolutions.

In one embodiment, temporary memory buffers are provided in the form of histograms each containing a number of histogram bins defined according to a value or range of values for a given physiological parameter. Physiological parameter values are stored in a temporary histogram bin having a definition matching the parameter value. Upon expiration of a storage interval, one or more statistical aspects are determined from the histogram data. For example, a median and upper and lower percentile values may be determined as the values assigned to the histogram bins containing the median, upper and lower percentile parameter values, respectively.

The bin values corresponding to the median and upper and lower percentile values may then be stored in a corresponding long-term memory buffer.

In one embodiment, each long-term memory buffer operates in association with two temporary memory buffers for storing sampled data on alternating storage intervals. Signal samples may be written during one storage interval to one temporary buffer while statistical analysis is performed on data that has been stored in the second temporary buffer during the previous storage interval and the statistical result is written to the long-term buffer.

DETAILED DESCRIPTION OF THE PREFERRED EMBODIMENTS

The present invention provides a method for acquiring, processing and storing multi-level time-resolved physiological data. The methods described herein are expected to be most beneficial when implemented in an implantable medical device wherein memory capacity is limited due to device size limitations. However, aspects of the present invention may also be beneficial when implemented in an external monitoring device, such as an ambulatory monitoring device wherein limited size for wearability or transportability by the patient imposes memory size restrictions.

Figure 1:
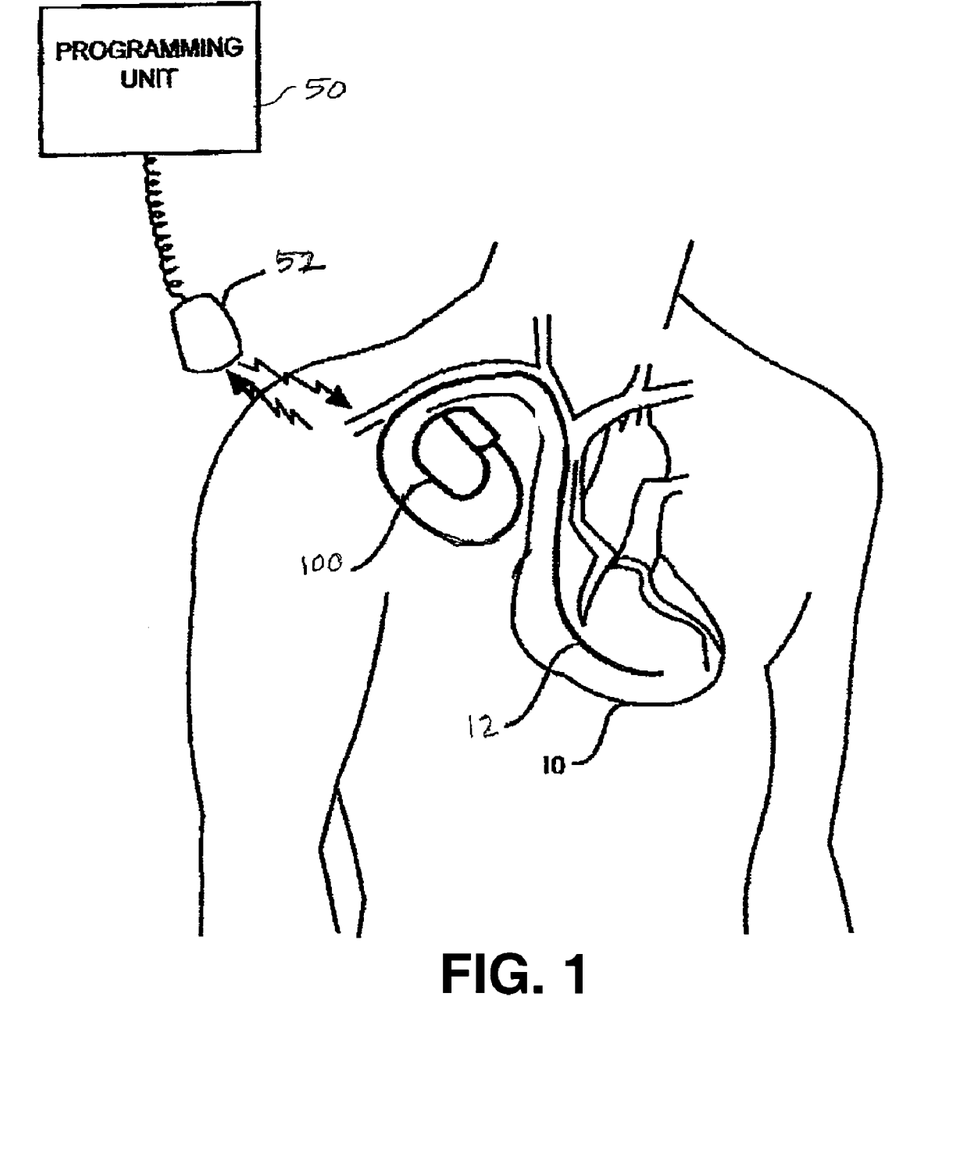
FIG. 1 is an illustration of an exemplary implantable monitoring device in which the present invention may be usefully practiced.

An exemplary implantable device in which the present invention may be usefully practiced is illustrated in FIG. 1. In the embodiment shown, device 100 is provided as an implantable device used for monitoring a patient's hemodynamic function. As such, device 100 is shown coupled to a lead 12 used for deploying one or more physiological sensors in operative relation to a patient's heart 10. Lead 12 is shown as a transvenous lead positioned intracardially in FIG. 1, however, a lead carrying one or more physiological sensors may alternatively be deployed in an epicardial, intravascular, subcutaneous or submuscular position for sensing cardiac-related physiological signals of interest. While the system shown in FIG. 1 includes a single lead 12, it is recognized that a system for monitoring physiological signals may include two or more leads, each of which may carry one or more sensors. Additionally or alternatively, device 100 may include physiological sensors located within or on the housing of device 100.

Furthermore, it is recognized that the methods presented herein for acquiring and storing physiological data may be beneficially employed in non-cardiac related monitoring applications and therefore require placement of a monitoring device and any associated leads equipped with physiological sensors at other internal body locations. Sensors that may be used for acquiring physiological data may include electrodes for sensing electrical signals or measuring tissue impedance, pressure sensors, flow sensors, temperature sensors, accelerometers, biochemical sensors such as oxygen sensors or pH sensors, or any other sensor known for use in monitoring a physiological activity or condition.

Device 100 may be embodied as a monitoring device with or without therapy delivery capabilities. With respect to cardiac-related applications, device 100 may be capable of providing electrical stimulation therapies such as cardiac pacing therapies, cardioversion, and or defibrillation therapies. In other embodiments, device 100 may include apparatus for delivering pharmaceutical agents.

Device 100 is preferably in telemetric communication with an external device 50 which couples to a programming head 52 for providing operable telemetry between the device 50 and the implanted device 100. External device 50 may be embodied as a "programmer," as well known in the art of cardiac pacemaker technology, for use in transmitting programming commands to and receiving data from the implanted device 100.

Figure 2:
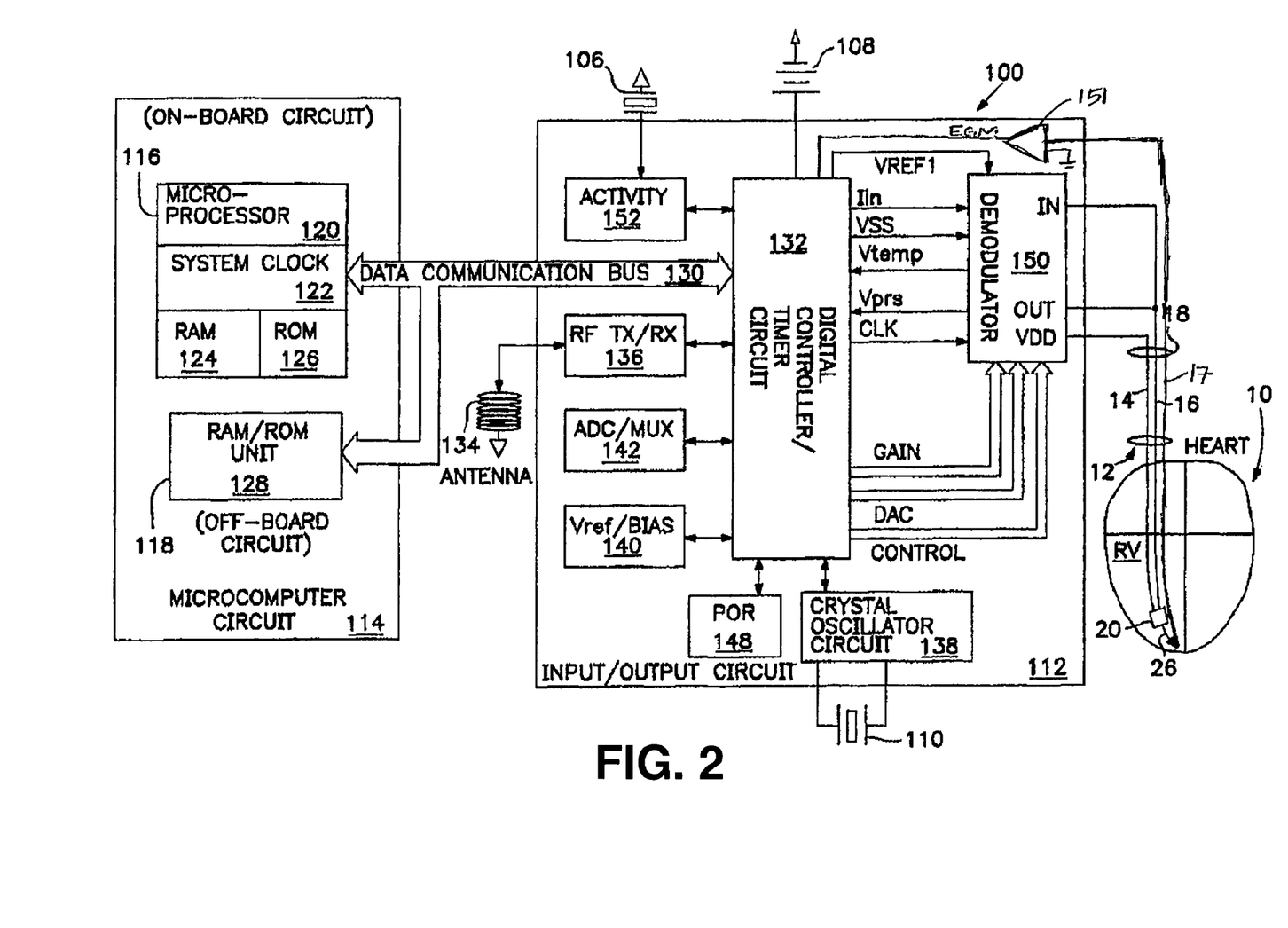
FIG. 2 is a functional block diagram of one embodiment of the monitoring device of FIG. 1 shown in conjunction with an associated lead in relation to a patient's heart.

FIG. 2 is a functional block diagram of one embodiment of the monitoring device of FIG. 1 shown in conjunction with an associated lead in relation to a patient's heart. Lead 12 has first and second lead conductors 14 and 16 extending from a proximal connector end 18 to a sensor 20 disposed near the distal lead end. In one embodiment, the sensor 20 is provided as a pressure sensor module for monitoring intra-cardiac pressure and temperature signals as generally described in the above-referenced U.S. Pat. Nos., 5,564,434 and 5,535,752. A third lead conductor 17 may be provided extending from an electrode 26 at or near the distal lead end to proximal connector end 18. The proximal connector assembly may be formed as an in-line multi-polar lead connector or a bifurcated lead connector and is coupled to device 100 via a conventional connector block assembly.

Device 100 is divided generally into an input/output circuit 112 coupled to a battery 108, an optional activity sensor 106, a telemetry antenna 134, the lead conductors 14,16, and 17, a crystal 110, and a microcomputer circuit 114. The input/output circuit 112 includes digital controller/timer circuit 132 and associated components including the crystal oscillator 138, power-on-reset (POR) circuit 148, Vref/BIAS circuit 140, analog-to-digital converter and multiplexor (ADC/MUX) circuit 142, RF transmitter/receiver circuit 136, optional activity circuit 152 and sensor signal demodulator 150.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer circuit 114 and demodulator 150. Power-on-reset circuit 148 responds to initial connection of the circuitry to the battery 108 for defining an initial operating condition and also resets the operating condition in response to detection of a low battery voltage condition. ADC/MUX circuit 142 digitizes analog signals received by digital controller/timer circuit 132 from demodulator 150 for storage by microcomputer circuit 114. When sensor 20 is provided as a pressure sensor module, signals are digitized by ADC/MUX circuit 142 corresponding to temperature (Vtemp) and pressure (Vprs) received from demodulator 150 as indicated in FIG. 2.

Data signals transmitted out through RF transmitter/receiver circuit 136 during telemetry are multiplexed by ADC/MUX circuit 142. Voltage reference and bias circuit 140, ADC/MUX circuit 142, POR circuit 148, crystal oscillator circuit 138 and optional activity circuit 152 may correspond to any of those presently used in currentlt marketed, implantable cardiac pacemakers.

The digital controller/timer circuit 132 includes a set of timers and associated logic circuits connected with the microcomputer circuit 114 through the data communications bus 130. Microcomputer circuit 114 contains an on-board chip 116 including microprocessor 120, associated system clock 122, and on-board RAM and ROM chips 124 and 126, respectively. In addition, microcomputer circuit 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which includes the periodic timing out of data sampling intervals for storage of monitored data, the transfer of triggering and data signals on the bus 130 and the receipt of programming signals. A real time clock and calendar function may also be included to correlate stored data to time and date.

Microcomputer circuit 114 controls the operating functions of digital controller/timer 132, specifying which timing intervals are employed during monitoring and during therapy delivery functions (if provided) and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM 124.

Data transmission to and from the external programmer 50 is accomplished by means of the telemetry antenna 134 and the associated RF transmitter and receiver 136, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. Uplink telemetry capabilities will typically include the ability to transmit stored digital information as well as real time physiological signals.

In accordance with the present invention, stored digital data that may be telemetered out will include multi-level time-resolved data relating to one or more physiological parameters. Such data may then be displayed in a graphical or tabular format by external programmer 50 or transferred to another external device such as a personal computer for display and analysis. Display of physiological parameters over varying time resolutions allows the physician to gain an overview of long-term and/or medium term trends, and study recent detailed data, most closely related to the patient's current condition. Such an evaluation of relatively long-term trends, short-term trends, and intermediate trends is generally in accord with a physician's diagnostic and prognostic thinking processes for many chronic conditions.

A number of power, timing and control signals are applied by the digital controller/timer circuit 132 to the demodulator 150 to initiate and power the operation of the pressure sensor module 20 and selectively read out the pressure and temperature signals Vprs and Vtemp. An active lead conductor 16 is attached through the connector block terminals to input and output terminals of demodulator 150 which supplies a voltage VREG at the output terminal. A passive lead conductor 14 is coupled through to the VDD supply terminal of the demodulator 150. The voltage signals Vprs and Vtemp developed from intervals between current pulses received at the input terminal are provided by demodulator 150 to the digital controller/timer circuit 132. The voltage signals Vprs and Vtemp are converted to binary data in an ADC/MUX circuit 142 and stored in RAM/ROM unit 128 in a manner well known in the art.

Input/output circuitry 112 further includes an EGM sense amplifier 152 which receives a signal from electrode 26 and using the monitor case as an indifferent electrode for acquiring an EGM signal. EGM sense amplifier 152 preferably takes the form of an automatic gain controlled amplifier with adjustable sensing threshold. The general operation of EGM sense amplifier 152 may correspond to that disclosed in U.S. Pat. No. 5,117,824, by Keimel, et al., incorporated herein by reference in its entirety. The EGM signal may be employed by timer circuit 132 to identify the onset of a cardiac depolarization in each heart cycle for deriving a heart rate and initiating monitoring and/or storage operations.

The lead 12 or a separate additional lead may be provided with an oxygen sensor module in the distal segment of the lead. Such a lead is shown in commonly assigned U.S. Pat. No. 4,750,495 to Moore and Brumwell, incorporated herein by reference an oxygen sensor demodulator and is also described in the above-incorporated '495 patent.

As indicated previously, device 100 may function as an interrupt-driven device wherein interrupt signals generated, which may be generated by digital controller/timer 132 at set time intervals or upon a particular device or patient-related event, "wake-up" microprocessor 120 to perform certain calculations or functions. In the acquisition of physiological parameter values, a sensor signal is continuously sampled and software included in microcomputer circuit 114 will be executed by microprocessor 120 upon generation of an interrupt signal to derive a physiological parameter from the digitized sensor signal data stored in a direct memory access (DMA) buffer. With regard to the embodiment shown in FIG. 2, right ventricular pressure and temperature and EGM signals are sampled at a nominal sampling frequency and the digitized signals are stored in DMA associated with microprocessor 120. An interrupt signal will also cause microprocessor 120 to increment an interrupt interval counter which may be used to time the various predetermined storage intervals associated with each of the temporary memory buffers used for storing physiological parameter data.

In accordance with the present invention, device 100 continuously stores parameterized physiological data in a number of temporary memory buffers corresponding to each of the desired temporal resolutions of each physiological parameter to be monitored. A portion of RAM 124 and/or RAM 128 of device 100 is designated for the temporary storage of physiological parameter values. Physiological parameter values are written to the appropriate temporary memory buffers included RAM 124 and/or RAM 128 under the control of microprocessor 120. Parameterized data are stored in a given temporary memory buffer for a predetermined storage interval. Upon expiration of the storage interval, statistical processing of the stored parameter values is executed by microprocessor 120 according to stored software algorithms.

One or more computed statistical aspects of the physiological parameter values are then written to an appropriate long-term, memory buffer designated in RAM 128 under the control of microprocessor 120. A long-term memory buffer is provided in association with each temporary memory buffer. Data stored in long-term memory buffers are available for uplinking to external device 50 (FIG. 1) via RF transmitter/receiver 136. If a long-term, memory buffer becomes full before a device interrogation is performed to uplink stored data, stored data may be overwritten by newly acquired data, preferably in a "first in, first out" format such that the oldest data value is overwritten by the newest value in an "endless" memory loop.

In a further variation, provision may be made for the patient to initiate permanent long-term storage of high-resolution physiological data, which might otherwise be overwritten in a long-term looping memory buffer designated for high resolution data. Through the use of an external programmer or a reed switch closure when an unusual event or symptom is experienced, a segment of high-resolution data stored in a long-term memory buffer beginning at a time prior to the patient-initiated trigger and extending for an interval thereafter may be stored in a designated area of permanent memory that will not be cleared or overwritten until uplinked to an external device. This high resolution physiological data stored upon patient initiation may be labeled by an event marker upon telemetry out for examination by the physician.

A number of physiological parameters of interest may be derived from a single digitized physiological sensor signal. For example, by positioning pressure sensor module 20 in the right ventricle for measuring right ventricular pressure, a peak or average systolic pressure, peak or average diastolic pressure, maximum rate of pressure development ($+dP/dt_{max}$), maximum rate of pressure loss ($-dP/dt_{min}$), and/or an estimated pulmonary artery diastolic pressure may be determined for each cardiac cycle. Furthermore, cardiac cycle-related time intervals may be derived from a pressure signal such as the pre-ejection interval and the systolic time interval. Thus, for a single physiological signal received, multiple physiological parameters may be derived, each of which may be designated for storage in multi-level time resolved temporary and long-term memory buffers.

Figure 3:
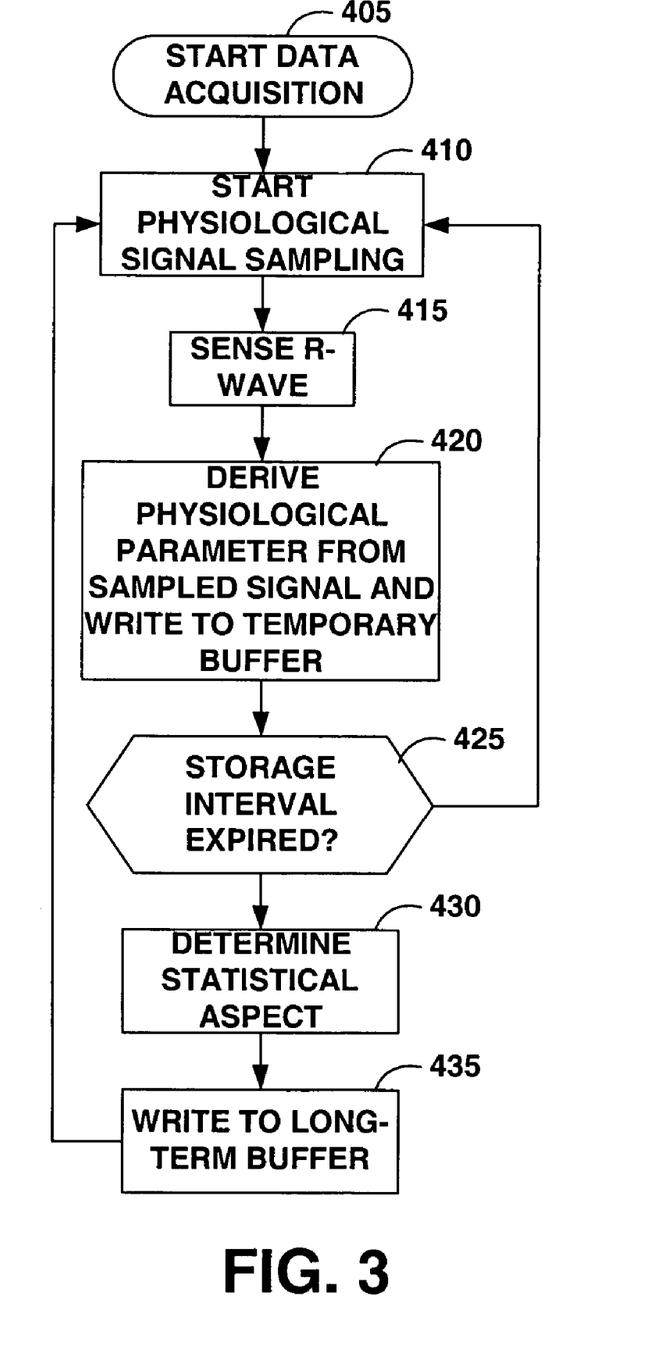
FIG. 3 is a flow chart providing an overview of steps included in a method for acquiring and storing physiological data according to one embodiment of the present invention.

FIG. 3 is a flow chart providing an overview of a method for acquiring and storing physiological data according to one embodiment of the present invention. At step 405, data acquisition is enabled through a programmer-entered command. Once enabled, signals from one or more physiological sensors are sampled at a desired sampling frequency at step 410. The sampling frequency may vary depending on the type of signal being sensed. For example, in a pressure sensor module provided as sensor 20 in FIG. 2, temperature may be sampled once every cardiac cycle and pressure may be sampled at a rate of 256 Hz. The sampling frequency selected may be fixed or programmable for a particular sensor signal and will depend on the resolution needed to achieve a meaningful resolution of derived, parameterized data.

With regard to cardiac monitoring applications, sensed signals may be parameterized on a beat-by-beat basis. For example, a pressure sensor signal sampled at a rate of 256 Hz may be used to derive one or more pressure-related parameters, as indicated previously, for each heart beat. In a preferred embodiment, a cardiac EGM signal is used to define cardiac cycle boundaries, for example by measuring R-R intervals. In FIG. 3, an R-wave is sensed at step 415 and physiological parameter(s) are derived from a digitized sensor signal and stored subsequently at step 420. Alternatively, cardiac cycle boundaries may be defined from mechanical signals, such as ventricular pressure. Physiological parameter values may be derived from digitized sensor signals on a less or more frequent basis than each cardiac cycle according to the type of monitoring application being performed. Cardiac-related or other types of physiological parameters may be determined based on sensor signals acquired over a defined interval of time, one or more cardiac cycles, one or more respiration cycles, etc.

At decision step 425, a determination is made whether a predefined storage interval has expired. As will be described in greater detail below, a designated temporary memory buffer is used to store parameterized signal data for a predefined storage interval. The length of the storage interval determines the degree of time resolution of the parameterized data that will be obtained and stored in a long-term memory buffer. If a storage interval has not expired at step 425, method 400 returns to step 410 to continue sampling the physiological signal and deriving and storing physiological parameter values in a temporary memory buffer.

Once a storage interval expires, as determined at decision step 425, at step 430 one or more statistical parameters are computed from the stored physiological parameter data. Computed statistical parameters may include, but are not limited to, an average, standard deviation, median, maximum, minimum and/or percentile. A computed statistical aspect from step 430 is then written to a long-term memory buffer at step 435.

It is the intention of the present invention to provide two or more long-term memory buffers designated for storing a statistical aspect of a particular physiological parameter at different time resolutions. Each long-term memory buffer is therefore associated with a temporary memory buffer which stores parameterized physiological data for a defined storage interval. The time resolution of statistical data stored in a long-term memory buffer will depend on the storage interval of the corresponding temporary memory buffer. A relatively short storage interval is defined to obtain fine resolution data; progressively longer storage intervals are defined for obtaining progressively coarser temporal resolutions in a multi-level time resolved storage format. For a given physiological parameter, multi-level time resolved data may be stored in a relatively fine resolution long-term memory buffer, a relatively course resolution long-term memory buffer, as well as one or more intermediate resolution long-term memory buffers.

Figure 4:
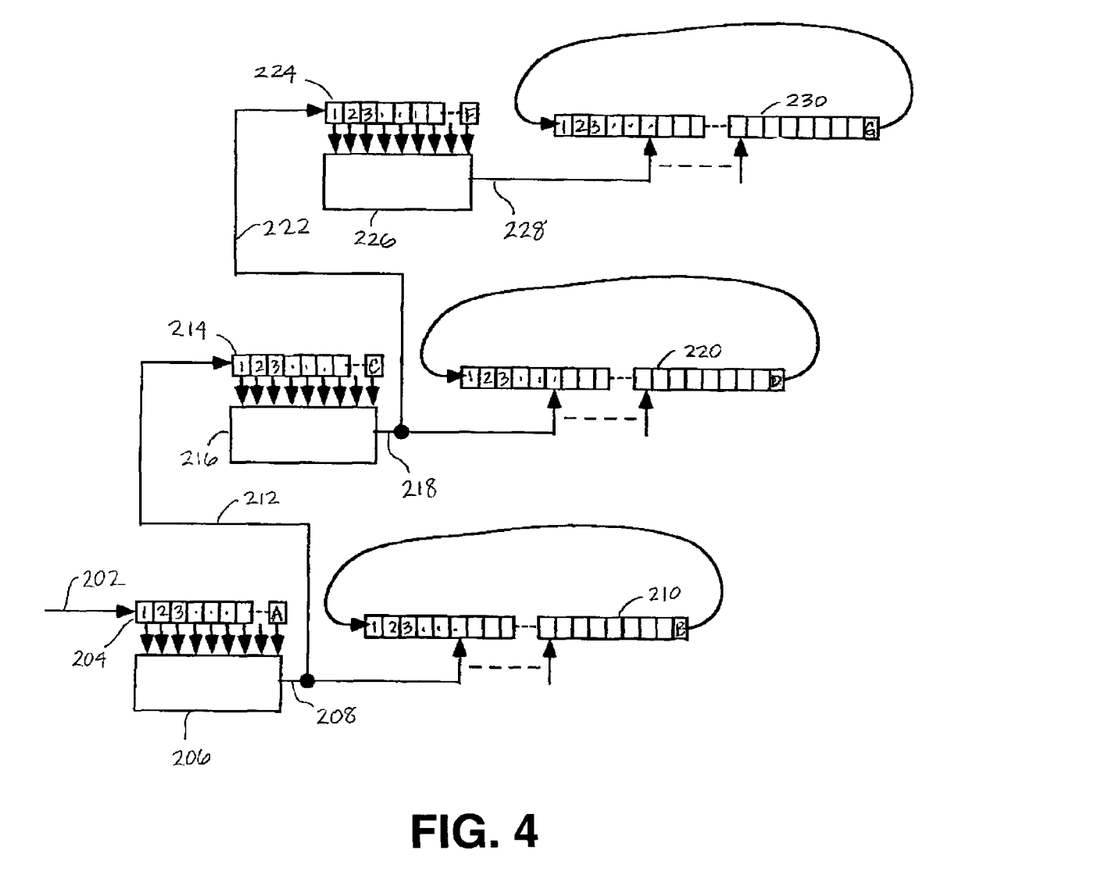
FIG. 4 is a schematic block diagram illustrating a method for memory allocation and physiologic data storage in a multi-level time-resolved data storage scheme according to one embodiment of the present invention in which multi-level temporary and long-term memory buffers are arranged serially.

FIG. 4 is a block diagram illustrating a method for memory allocation and physiologic data storage in a multi-level time-resolved data storage scheme according to one embodiment of the present invention. In FIG. 4, parameterized physiological data are provided as input 202 to a temporary memory buffer 204 which stores a number, A, of parameterized physiological data points. The number of points stored will depend on a programmable storage interval and the sampling frequency of the parameterized data.

A storage interval may be defined as an interval of time such as a few seconds, a few minutes, a few hours, etc. Alternatively, a storage interval may be defined according to a number of cardiac cycles or respiration cycles or according to a desired number of parameterized data points. The storage interval is preferably programmable and, in one embodiment, ranges from 2 seconds to three months, wherein shorter storage intervals are selected to achieve fine temporal resolution and longer storage intervals are selected to achieve intermediate or coarse temporal resolution.

Temporary memory buffer 204 shown in FIG. 4 is associated with a fine resolution long-term memory buffer 210 and is therefore expected to be assigned a relatively short storage interval, e.g., a few seconds or a few minutes. Upon expiration of the storage interval, a statistical feature of the parameter values stored in temporary buffer 204 is determined at processing block 206. Digital signal processing may be used for determining an average, median, maximum, minimum, percentile or other statistical aspect of the stored data. Such processing may be performed by dedicated circuitry or by algorithms executed by microprocessor 120. The statistical result provided as output 208 from block 206 is then written to fine-resolution, long-term memory buffer 210. The capacity of the fine-resolution, long-term memory buffer 210 is preferably selectable. Finely-resolved data may be stored, for example, for several minutes, one or more hours, one or more days, or longer depending on the rate of deriving a physiological parameter from a sampled signal and the selected storage interval assigned to temporary memory buffer 204, both of which will depend in part on the nature of the data to be stored.

Fine-resolution, long-term memory buffer 210 is preferably provided as a looping memory buffer such that once memory buffer 210 is full, the oldest statistical value stored is overwritten by the newest statistical value. Recent physiological data will generally be of greater interest to a clinician than relatively older data. Thus the number of statistical values, B, stored in fine-resolution, long-term memory buffer 210 will depend on the storage interval of temporary memory buffer 204 and a programmed loop duration of long-term memory 210. For example, the storage interval for temporary buffer 204 may be 1 minute, and the long-term memory buffer 210 may be programmed to store 24 hours of data in a continuous looping fashion such that up to 1,440 statistical values computed from one minute of parameterized data will be stored in fine-resolution, long-term memory buffer 210.

The output 208 of data processing block 206 is further provided via conductor 212 as an input to a second memory buffer 214 designated as a medium-resolution temporary memory buffer. Medium-resolution temporary memory buffer 214 receives and stores a number, C, (via conductor 212) of statistical values from processing block 206. The number of values, C, stored by medium-term temporary memory buffer 214 is determined according to a selectable, preferably programmable, medium-term storage interval and the resolution of the finely-resolved statistical feature determined by block 206. For example, if the fine-resolution storage interval is set to one minute, a medium-resolution storage interval may be set to one hour. As such, medium-resolution temporary memory buffer 214 will receive 60 statistical values from output 208 of processing block 206.

Processing block 216 will, in turn, determine a statistical aspect of the C values stored in medium-resolution temporary memory buffer 214 at the end of the medium-resolution storage interval and provide the statistical value as output 218 to be received by a medium-resolution long-term memory buffer 220. Medium-resolution long-term memory buffer 220 is also preferably provided as a continuous loop memory buffer, the capacity of which is preferably programmable. For example, if the medium-resolution storage interval is set for 1 hour, long-term memory buffer 220 may be set to store one month, or 672, hourly statistical values. Thus the number of values, D, stored in medium-resolution, long-term memory buffer 220 will depend on the selected duration of the memory loop and the medium-resolution storage interval.

The output 218 of medium-resolution processing block 216 is further provided via conductor 222 as input to a coarse-resolution temporary memory buffer 224. A number, F, of medium-resolution data values may be stored in coarse-resolution temporary memory buffer 224. The number of values stored in coarse-resolution temporary memory buffer 224 will depend on a selectable coarse-resolution storage interval and the resolution of the medium-resolution values received as input. Continuing the example provided above wherein a medium-resolution storage interval was set as one hour, a coarse-resolution storage interval may be set to 24 hours such that upon expiration of a 24-hour storage interval a daily statistical value may be determined by processing block 226.

The coarse resolution statistical value provided as output 228 is written to a coarse-resolution long-term memory buffer 230. Long-term memory buffer 230, which is preferably a continuous loop memory buffer of programmable length, is capable of storing G coarse-resolution statistical values, where the number of values, G, will depend on the coarse-resolution storage interval and the programmed coarse-resolution long-term memory loop duration. For example, the duration of long-term memory loop 230 may be programmed to be 365 days to allow storage of daily statistical values for up to one year.

Thus in the current example, 1-minute statistical values for the most recent 24 hours are available from the fine-resolution long-term memory buffer 210; hourly statistical values are available for the most recent month from the medium-resolution, long-term memory buffer 220; and daily statistical values are available for up to one year from the coarse-resolution, long-term memory buffer 230.

One advantage of continuously acquiring and storing fine-resolution data is that a detailed "picture" of the most recent physiological data is available whenever a symptomatic event occurs or a clinical test is performed without requiring reprogramming of the physiological data storage parameters. For example, a patient may be advised to perform a clinical test such as a 6-minute walk or a stair-climbing, treadmill, or stationary bicycle exercise test. The physiological data during such a test may be immediately available for transmission from an implanted device to an external device. An external device receiving transmitted data may be, for example, an external physician programmer, a patient programmer or home monitor which may be in communication with a centralized, physician-accessible data base, a personal computer, a centralized computer network system, or an Internet based patient data system via a modem. Hence, the physician may easily obtain finely resolved physiological data from a recent test or symptomatic event.

The physiological data storage method illustrated by the schematic diagram of FIG. 4 represents a serial arrangement of multi-level, time-resolved physiological data wherein coarsely resolved data values are determined from more finely resolved data values. In this "nested" arrangement, the allocation of memory and the resolution of lower-resolution memory buffers will depend in part on the resolution and memory allocation of higher-resolution memory buffers. If a relatively long duration of fine resolution data is desired, the memory available for medium and coarsely resolved data will be more limited. If a fixed amount of memory is available for storing physiological data, the memory available for each resolution level of a given statistical aspect of a particular physiological parameter will be interdependent on the number of physiological parameters selected for data storage and the duration and resolution of each long-term memory buffer.

During a programming procedure for enabling data acquisition, a physician would assign storage intervals and long-term memory durations for selected physiological parameters to be stored in multiple temporal resolutions. Software included in the programming device is expected to perform calculations of remaining memory available as the programming proceeds. For example, once a fine-resolution storage interval and long-term memory duration are selected, indications are made to the physician regarding the long-term memory durations that are available for each of the possible storage interval selections for intermediate or coarse resolution storage levels. Such indications may be made in a tabular format or by a message that indicates the maximum long-term storage duration available if the shortest storage interval is selected for a given storage level.

Figure 5:
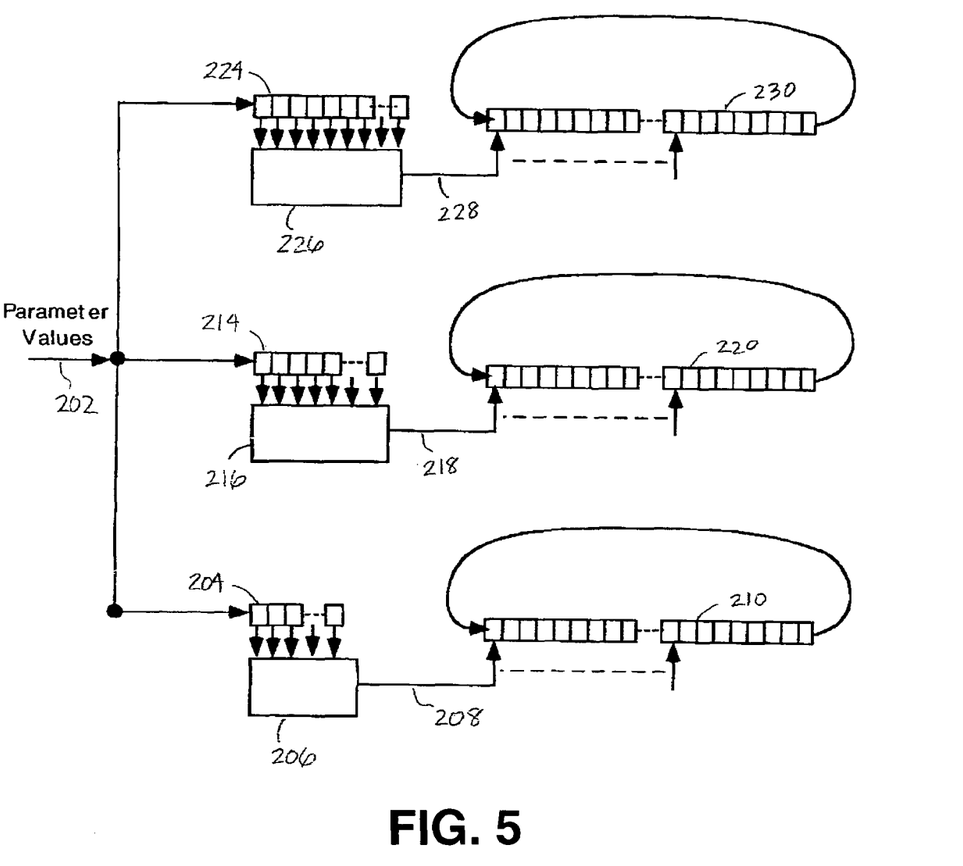
FIG. 5 is a schematic block diagram illustrating a method for allocating memory and storing multi-level time-resolved physiological data according to a parallel arrangement of multi-level temporary and long-term memory buffers.

FIG. 5 is a schematic block diagram illustrating a method for allocating memory and storing multi-level time-resolved physiological data according to an alternative embodiment of the present invention. The method shown in FIG. 5 illustrates a parallel arrangement for storing multi-level time-resolved data. In this embodiment, parameterized data points are received directly as input 202 for storage in each resolution level of temporary memory buffers 204, 214, and 224. Fine-resolution memory buffer 204 stores a number, A, of physiological parameter values received as input 202 for a fine-resolution storage interval, after which a statistical aspect is determined from the stored values by processing block 206 and provided as output 208 to be written to fine-resolution long-term memory loop 210.

In a similar manner, medium- and coarse-resolution temporary memory buffers 214 and 224, respectively, receive and store a number of physiological parameter values received directly from input 202. Parameter values are stored for a medium-resolution storage interval in temporary memory buffer 214 after which a medium-resolution statistical value is determined by processing block 216 and written to medium-resolution long-term memory loop 220. Parameter values are stored for a coarse-resolution storage interval in coarse-resolution temporary memory buffer 224 and a coarse-resolution statistical value is determined by processing block 226 and written to coarse-resolution long-term memory loop 230. The medium- and coarse-resolution statistical values determined at blocks 216 and 226 and stored in the medium- and coarse resolution memory loops 220 and 230 do not depend on the fine-resolution data 208 as input.

The parallel arrangement of multi-level resolved data storage as shown in FIG. 5 simplifies the selection of the storage intervals for coarser resolved data storage since these selections are not dependent on the resolution of finer-resolution storage levels. The statistical values stored in the medium-term and long-term resolution memory loops will be more accurate since these values will have been determined directly from sampled parameter values rather than statistical values determined at the next finer resolution level. However, the parallel arrangement may not be as computationally or power efficient as the serial arrangement described in conjunction with FIG. 4, and the parallel arrangement will require greater temporary buffer storage capacity for storing sampled parameter values for relatively long storage intervals in the medium- and coarse-resolution temporary memory buffers.

While the methods described in conjunction with FIGS. 4 and 5 relate to three levels of time-resolved data, fine, medium and coarse, it is recognized that, for a given physiological parameter, two or more levels of time-resolved data may be designated. Furthermore, it is recognized that for a given storage interval, multiple statistical and/or other mathematical, time or frequency domain parameters may be determined from the data stored in a given temporary memory buffer and written to a corresponding long-term memory buffer. For example, any of the average, median, desired percentile value, standard deviation, maximum, minimum, or other value derived from the stored sample points may be written to a corresponding long-term memory buffer.

Figure 6:
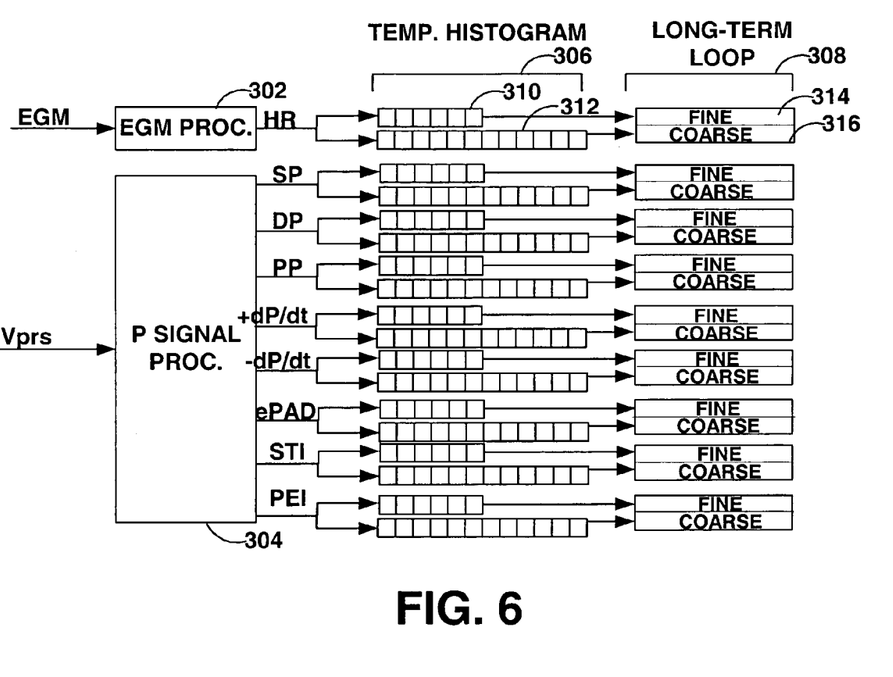
FIG. 6 is a schematic block diagram of one method for determining and storing multi-level resolved median and percentile values of sampled physiological data using temporary histograms in association with each long-term memory buffer.

FIG. 6 is a schematic block diagram of one method for determining and storing multi-level resolved median and percentile values of sampled physiological data. The inventors of the present invention have found that the storage of median values of hemodynamic related data acquired from an intracardiac pressure sensor may be of greater interest than the storage of average values because the storage of median values effectively eliminates the effect of "outliers" among the sampled data points which may otherwise produce anomalous average values. As such, a median value of a series of sequentially acquired physiological data points may be determined by temporarily storing a number of sampled data points in a histogram format, then determining the histogram bin in which the median data point resides at the end of a predetermined storage interval.

As noted previously and as shown in FIG. 6, one or more physiological parameters may be derived from a given physiological signal. In the embodiment shown in FIG. 6, and with regard to the device shown in FIG. 2, an EGM signal is received and processed at block 302 for deriving a heart rate (HR). The heart rate may be expressed in terms of the R-R interval measured between consecutively sensed R-waves of the EGM signal. Digital controller/timer 132 (FIG. 2) may derive an R-R interval based on the time between R-out signals received from sense amplifier 151 (FIG. 2). Alternatively, a digitized EGM signal may be processed by microprocessor 120 (FIG. 2) for deriving R-R intervals or other EGM intervals or characteristics that may be of interest such as R-T intervals, P-R intervals, R-wave amplitude, R-wave duration, etc.

A ventricular pressure signal (Vprs), typically a right ventricular pressure signal, is received and processed at block 304 for deriving a number of ventricular pressure-related hemodynamic parameters which may include, but are not limited to: systolic pressure (SP), diastolic pressure (DP), pulse pressure (PP), maximum rate of pressure development (+dP/dt), minimum rate of pressure development (−dP/dt), estimated pulmonary artery diastolic pressure (ePAD), a systolic time interval (STI) and a pre-ejection time interval (PEI). Microprocessor 120 (FIG. 2) may perform signal processing algorithms represented by signal processing block 304 for deriving each of these pressure-related parameters from a digitized pressure signal.

The heart rate (or R-R interval) and each of the pressure-related parameters of interest may be determined on a beat-by-beat basis as described previously. A bank of temporary histograms 306 and associated long-term looping memory buffers 308 are provided for storing parameterized data and statistical aspects of parameterized data, respectively. In the embodiment of FIG. 6, a fine-resolution temporary histogram 314 having a short storage interval and a coarse-resolution temporary histogram 316 having a relatively long storage interval are provided for receiving and temporarily storing derived physiological parameter values received from signal processing blocks 302 or 304. For example, a fine-resolution temporary histogram 310 having a short storage interval and a coarse resolution temporary histogram 312 having a relatively long storage interval are provided for receiving and storing heart rate data from signal processing block 302. Physiological parameters will be stored in respective temporary histograms 314, 316 for the designated storage interval, defined according to the temporal resolution desired as described previously. Multiple temporary histograms may be provided for a given physiological parameter with each temporary histogram having a uniquely defined storage interval for achieving relatively fine and coarse temporal resolutions 314, 316 as shown in FIG. 6, and may further include any number of intermediate resolution temporary histograms (not shown in Fig 6.

Values for a particular physiological parameter are stored in an appropriate histogram bin provided in a respective temporary histogram included in bank 306 according to histogram bin definitions. A bin definition defines a value or range of values of the corresponding physiological parameter. A derived parameter value is thus stored in the bin having a definition that matches the parameter value. Parameter values not matching any bin definition may be considered outliers and be discarded. At the end of the storage interval, the bin containing the median percentile value is identified such that the bin value may be written to a corresponding long-term memory loop included in bank 308. In one embodiment, a median and upper and lower percentile values are determined from stored histogram data at the end of a storage interval and written to a corresponding long-term memory loop included in memory loop bank 308.

A median histogram bin value may be determined as the value of the bin in which the $i^{th}$ parameter value is stored where:

$i=\{$(total number of parameter values stored)$/2\}+1$.

According to one embodiment, the median histogram bin value may then be identified at the end of a storage interval by summing the number of values stored in each histogram bin beginning with the lowest histogram bin until the sum is greater than i. The histogram bin that causes the sum to be greater than i will contain the median parameter value. This histogram bin value or a number designating the bin may be written to a respective long-term memory buffer.

In addition, upper and lower percentile histogram bin values may be stored wherein the upper and lower percentile values to be determined are programmable. For example, the histogram bin containing the $5^{th}$ percentile parameter value and the $95^{th}$ percentile parameter value may be determined and the corresponding bin number stored. For a given percentile, n, the number of parameter values less than the $n^{th}$ percentile may be determined by multiplying the total number of parameter values stored during a storage interval by n %. The $n^{th}$ percentile value may then be determined by summing the number of parameter values stored in each histogram bin beginning at the lowest histogram bin until the number of parameter values less than the $n^{th}$ percentile is exceeded. The histogram bin that causes the sum to exceed this number includes the $n^{th}$ percentile value. The histogram bin value or a number identifying the bin associated with the $n^{th}$ percentile value may then be written to a corresponding long-term memory buffer included in bank 308.

Figure 7:
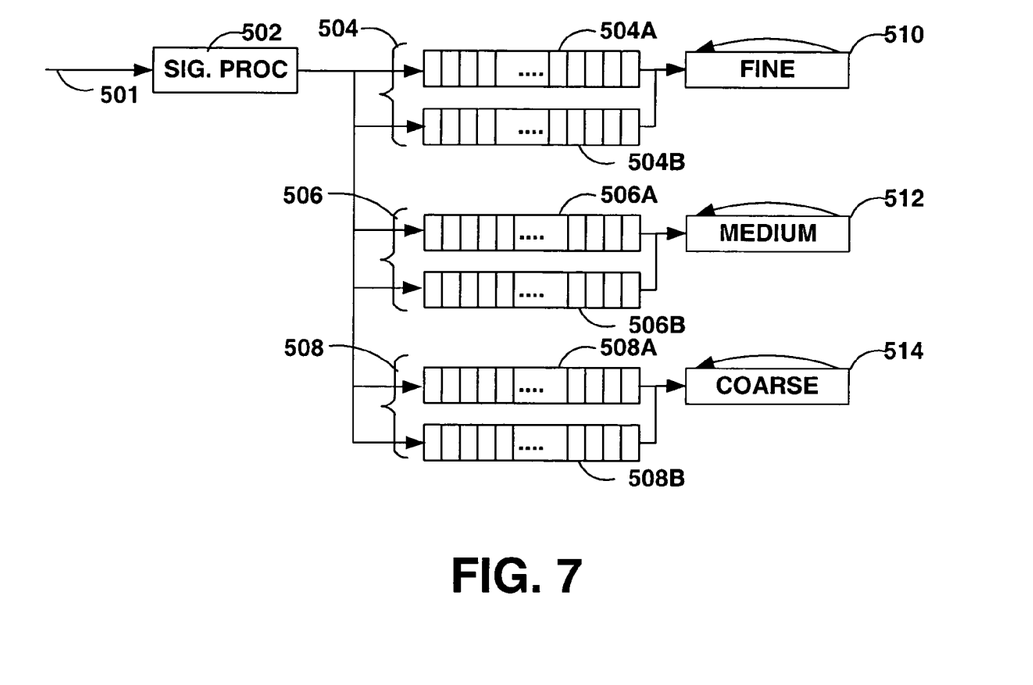
FIG. 7 is a block diagram illustrating an alternative method for acquiring and storing multi-level time-resolved physiological data which includes pairs of temporary memory buffers associated with each long-term memory buffer.

FIG. 7 is a block diagram illustrating a scheme for storing multi-level time-resolved physiological data according to an alternative embodiment of the present invention. In FIG. 7, each long-term memory buffer 510, 512, and 514 is associated with a pair of temporary memory buffers 504, 506, and 508, respectively, which may be in the form of temporary histograms as described above. A physiological sensor signal 501 is received by signal processing block 502 and a parameterized signal value provided as output from signal processing block 502 is written to the first buffer 504A, 506A and/or 508A, of a given pair of temporary memory buffers 504, 506, and/or 508. Once the first buffer is filled, at the end of a corresponding storage interval, parameterized signal data received from signal processing block 502 is written to the second temporary memory buffer 504B, 506B, and/or 508B, of a given pair 504, 506, or 508.

While parameterized data is being continuously written to the second temporary memory buffer, 504B, 506B, and/or 508B, a statistical aspect of the stored data is computed from the data stored in the first temporary memory buffer 504A, 506A, and/or 508A and stored in an associated long-term memory buffer 510, 512 or 514. The first temporary memory buffer 504A, 506A, and/or 508A, may then be cleared of data. Meanwhile, parameterized signal data continues to be written to the second temporary memory buffer 504B, 506B, and/or 508B included in a temporary memory buffer pair 504, 506, and/or 508, until the next storage interval expires, after which parameterized signal data will be written again to the first temporary memory buffer 504A, 506A, and/or 508A while statistical computations are performed on the values stored in the second temporary memory buffer 504B, 506B, and/or 508B. Thus, parameterized data may be written to a temporary memory buffer on alternating storage intervals to allow statistical computations and writing to long-term memory buffers to be performed while still continuously acquiring and storing parameterized data.

Thus, a system and method have been described for acquiring and storing physiological data in multiple levels of temporal resolution. While particular embodiments of the present invention have been described herein, it is recognized that numerous variations could be conceived by one having skill in the art and the benefit of the teachings provided herein. The detailed descriptions provided are intended to be exemplary, therefore, rather than limiting with regard to the following claims.

What is claimed is:

1. A method performed by a processor for storing and processing physiological mechanical data in an implantable medical recording device, the method comprising:
    sampling one or more physiological signals at a selected sampling rate;
    deriving physiological parameter values from the sampled signal to obtain parameterized signal data at a rate lower than the selected sampling rate of the physiological signal;
    storing the parameter values as they are determined in a temporary memory buffer for a predetermined storage interval;
    determining a statistical aspect of the stored parameter values in the temporary buffer upon expiration of the storage interval; and
    writing the statistical aspect as it is determined for a plurality of the predetermined storage intervals to a long-term memory buffer, the long-term memory buffer storing the statistical aspects for a long-term storage interval, the long-term memory buffer thereby storing statistical aspects having a temporal resolution of the parameter values corresponding to the predetermined storage interval of the temporary memory buffer, further comprising:
    allocating the temporary memory buffer into at least two different temporary memory buffers and programming a unique storage interval to each of the two different temporary memory buffers.

2. A method according to claim 1, further comprising allocating the long-term memory buffer into at least two different long-term memory buffers each having a unique temporal resolution, wherein the unique temporal resolution of each long-term memory buffer is determined by the predetermined storage interval of a respective one of the temporary memory buffers.

3. A method according to claim 2, wherein the at least two long-term memory buffers comprise digital memory buffers.

4. A method according to claim 2, wherein the unique temporal resolution comprises at least a one of: a coarse resolution having a relatively low temporal resolution, a medium resolution having a higher temporal resolution than said course resolution, and a fine resolution having the highest temporal resolution compared to said coarse resolution and said medium resolution.

5. A method according to claim 4, wherein upon expiration of a predetermined storage interval or upon exceeding available memory storage of a given long-term storage buffer the following step is performed:
    transferring a set of data comprising the statistical aspect or the stored parameter values from one of said fine resolution and said medium resolution to said coarse resolution and from said fine resolution to said medium resolution.

6. A method according to claim 4, further comprising:
    allocating available memory for the stored parameters based at least in part upon a respective temporal resolution assigned to each of the stored parameters, wherein said respective temporal resolution comprise said coarse resolution, said medium resolution, said fine resolution.

7. A method according to claim 6, wherein the allocating further comprises automatic partitioning of available memory based upon the number of stored parameters or the temporal resolution of the stored parameters.

* * * * *